(12) United States Patent
Kurkin et al.

(10) Patent No.: US 8,630,808 B2
(45) Date of Patent: Jan. 14, 2014

(54) ESTIMATION OF DIAGNOSTIC MARKERS

(75) Inventors: Sergey Kurkin, Eindhoven (NL); Bart Jacob Bakker, Eindhoven (NL); Rene Van Den Ham, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 287 days.

(21) Appl. No.: 12/682,800

(22) PCT Filed: Oct. 14, 2008

(86) PCT No.: PCT/IB2008/054214
§ 371 (c)(1),
(2), (4) Date: Apr. 13, 2010

(87) PCT Pub. No.: WO2009/050643
PCT Pub. Date: Apr. 23, 2009

(65) Prior Publication Data
US 2010/0241359 A1    Sep. 23, 2010

(30) Foreign Application Priority Data

Oct. 16, 2007 (EP) ..................................... 07118550

(51) Int. Cl.
*G01N 33/48* (2006.01)

(52) U.S. Cl.
USPC .......................................................... 702/19

(58) Field of Classification Search
USPC .......................................................... 702/19
See application file for complete search history.

(56) References Cited

U.S. PATENT DOCUMENTS

| 6,099,469 A | 8/2000 | Armstrong et al. |
| 6,306,087 B1 * | 10/2001 | Barnhill et al. ............... 600/300 |
| 2001/0023419 A1 | 9/2001 | Lapointe |
| 2003/0143572 A1 | 7/2003 | Lu et al. |
| 2006/0121619 A1 | 6/2006 | Bowser |
| 2006/0259246 A1 | 11/2006 | Huyn |
| 2007/0005261 A1 | 1/2007 | Serena et al. |

FOREIGN PATENT DOCUMENTS

| WO | 9201065 A1 | 1/1992 |
| WO | 9505590 A1 | 2/1995 |
| WO | 9918442 A1 | 4/1999 |
| WO | 0052199 A1 | 9/2000 |
| WO | 2005036446 A2 | 4/2005 |
| WO | 2006002240 | 1/2006 |
| WO | 2006072011 A2 | 7/2006 |
| WO | 2006100346 S1 | 9/2006 |

OTHER PUBLICATIONS

Jennings et al. "Multilaboratory Testing in Thrombophilia Through the United Kingdom National External Quality Assessment Scheme (Blood Coagulation) Quality Assurance Program," Seminars in Thrombosis and Hemostasis (2005) vol. 31, No. 31, pp. 66-72.*
Chandler et al. "Estimating the Rate of Thrombin and Fibrin Generation in vivo During Cardiopulmonary Bypass" Blood (2003) vol. 101, pp. 4355-4362.*
Ellenius et al: "Neural Network Analysis of Biochemical Markers for Early Assessment"; Medical Informatics Eruope '97; vol. 1, pp. 382-385.
Baglin, Trevor "The Measurement and Application of Thrombin Generation" British Journal of Haematology, vol. 130, 2005, pp. 6523-6661.

* cited by examiner

*Primary Examiner* — Jerry Lin

(57) ABSTRACT

A method for estimating concentrations or concentration changes of particular biological markers, e.g. proteins, includes performing estimations by providing a mathematical model with data from measurements of other biological markers, e.g. other proteins. Thus, instead of measuring the concentration of particular proteins, this concentration can be estimated using the model. The estimated proteins can be used together with other clinical data in another model which is able to provide information or estimations of a patient's disease, for example.

20 Claims, 2 Drawing Sheets

ESTIMATION OF DIAGNOSTIC MARKERS

FIELD OF THE INVENTION

The invention relates in general to a method for estimating biological markers, in particular to estimating biological markers from measured biological markers using a model.

BACKGROUND OF THE INVENTION

It is well known to use various biomarkers, such as measurement of blood pressure, or measurements of biological material such as proteins for helping the clinician in making a diagnosis. However, measurement of several proteins may be technically difficult or even impossible since bio-assays for measuring a particular biomarker may not even be available.

Thus, due to technical difficulties or economic considerations using several or expensive bio-assays, it is difficult or impractical to measure several biomarkers However, in order to obtain a reliable diagnosis it may be necessary to measure several biomarkers.

WO 2006/002240 discloses a method for constructing classifiers that distinguish between trait subgroups using molecular marker data from blood samples. The invention further encompasses the use of the classifiers and combinations of molecular markers identified by the classifiers in a wide variety of applications including: diagnosis; prognosis; prediction of disease, stage of disease or disease risk. The invention further provides a variety of selected molecular markers and a means to identify combinations of the selected molecular markers useful for diagnosing particular traits of interest.

Accordingly, WO 2006/002240 succeeds in identifying particular molecular markers that are useful for diagnosing. However, WO 2006/002240 does not succeed in simplifying the task of suggesting a diagnosis, since the requirement to measure all molecular markers for making a diagnosis may require different bio-assays, may be time consuming and may stress the patient.

SUMMARY OF THE INVENTION

Accordingly, the invention preferably seeks to mitigate, alleviate or eliminate one or more of the above mentioned problems singly or in any combination. In particular, it may be seen as an object of the present invention to provide a method and an apparatus capable of simplifying the task of suggesting a diagnosis or provide information which is useful for making a diagnosis or determining other conditions of a patient. This is achieved by providing a method for determining an estimated biological marker from a measured biological marker.

This object and several other objects are obtained in a first aspect of the invention by providing a method according to the independent claims.

The invention is particularly, but not exclusively, advantageous for estimating a biological marker from a measured biological marker.

Accordingly, an embodiment of the first aspect of the invention relates to a method for determining an estimated biological marker from a measured biological marker, where the method comprises, receiving input data representing the measured biological marker, processing the input data using a biological model for determining the estimated biological marker, providing the estimated marker via an output device.

Thus, by measuring only one or more biological markers, for example proteins, the method enables determining other one or more estimated biological markers on basis of the measured markers. Thus, it may be an advantage that it is not necessary to measure all biological markers for providing sufficient information for enabling the determination of a condition of a patient since some of the required biological markers can be estimated from one or more measured biological markers. For example, it may be technically difficult to measure a particular biological marker and, therefore, it may be desirable to estimate that particular biological marker from other measured markers. Also, it may be an advantage that the patient does not need to be exposed to numerous sample takings.

The measured biological marker may have been obtained from a biological sample—that is, it may have been obtained from previous analysis of biological samples which have been removed from a patient. The measured biological marker may also have been obtained from databases containing lists of measured data. Alternatively, the measured biological marker may have been obtained by using a medical score (score given by a medical professional that can be based on his/her own knowledge and experience) in order to estimate a possible range (if those ranges are known to exists from the previous studies by identifying the correlation between those markers and the score) of a particular biological marker.

It is understood that providing the estimated marker via an output device may comprise generating a signal representing the one or more estimated markers or providing the estimated marker on a display, for example as a list of data.

The biological markers may comprise biological markers selected from the list comprising: proteins, metabolites, genetic polymorphisms, gene copy number variations, or any other molecular entity that can be correlated with the end protein state, its iso form or the protein complex.

In an embodiment the biological model may be a model capable of modeling kinetic interactions between different biological markers. For example, the biological model may be capable of describing the relation between change of concentration of one protein when the concentration of another protein changes.

In an embodiment the input data further comprises clinical data selected from the list comprising, but not limited to: age, sex, current or previous diseases, current or previous therapies, dosages of therapeutic drugs and measured biological factors. It may be an advantage that the method is capable of receiving and processing other input data than only biological markers. Thus, by receiving and processing other clinical data, for example a measured blood pressure, the biological model may be able to estimate biological markers with greater accuracy, or some of the estimated biological markers may be precluded using knowledge of the clinical data, for example if the estimated biological markers does not fit within the constraints of the additional clinical data. Accordingly, the additional clinical data may be used for constraining a plurality of estimations by precluding incorrect estimations.

In an embodiment the method of receiving input data comprises receiving first input data and receiving second input data, wherein the first and second input data are received at different points in time. Accordingly, by consecutively receiving input data—that is, by initially receiving first input data, then after a period of time receiving second input data and so on—a series or history of input data is obtained. Such history of input data may improve the capability of the biological model to estimate biological markers with greater accuracy since the model is gradually adapted to the particular patient. Since input data may be processed each time new input data are provided, either the entire history of input data or a fraction of the history may be processed when new input data arrives, or only the most recent input data is processed when it arrives.

In an embodiment the measured biological marker is a concentration of a biological marker, alternatively a change in the concentration of the biological marker.

Similarly, in an embodiment the estimated biological marker is a concentration of the biological marker, alternatively a change in the concentration of the biological marker.

In an embodiment the method further comprises the step of estimating a patient condition using the patient data comprising one or more of the measured biological marker, the estimated biological marker and clinical data, wherein the estimation of the patient condition comprises processing said patient data using a patient condition model which relates said patient data to patient conditions. Thus, when the estimated biological markers have been determined, the patient condition may be estimated or otherwise inferred from the patient data.

In a second aspect, the invention relates to a medical apparatus according to the independent claims.

In a third aspect, the invention relates to a clinical system comprising a medical apparatus according to the second aspect and a patient condition apparatus comprising processing means for estimating a patient condition using the patient data. The patient condition apparatus may also comprise an output for providing the patient condition as a signal or information on a display. In an embodiment the clinical system may further comprise an analyzing device for receiving a biological sample, processing the sample and providing a measured biological marker.

In a fourth aspect, the invention relates to a computer program product being adapted to enable a computer system comprising at least one computer having data storage means associated therewith to perform the method according to the first aspect of the invention.

This aspect of the invention is particularly, but not exclusively, advantageous in that the present invention may be implemented by a computer program product enabling a computer system to perform the operations of the second aspect of the invention. Such a computer program product may be provided on any kind of computer readable medium, e.g. magnetically or optically based medium, or through a computer based network, e.g. the Internet.

The first, second, third and fourth aspects of the present invention may each be combined with any of the other aspects. These and other aspects of the invention will be apparent from and elucidated with reference to the embodiments described hereinafter.

In summary the invention relates to a method for estimating concentrations or concentration changes of particular biological markers, e.g. proteins. Thus, the method enables making statements about for example diagnostic blood markers (e.g. their concentrations and properties) without directly measuring them. The estimations are performed by providing a mathematical model with data from measurements of other biological markers, e.g. other proteins. Thus, instead of measuring those particular proteins they can be estimated using the model. The estimated proteins can be used together with other clinical data in another model which is able to provide information or estimations of, for example, a patient's disease.

BRIEF DESCRIPTION OF THE FIGURES

The present invention will now be explained, by way of example only, with reference to the accompanying Figures, where.

DETAILED DESCRIPTION OF AN EMBODIMENT

Figure 1:
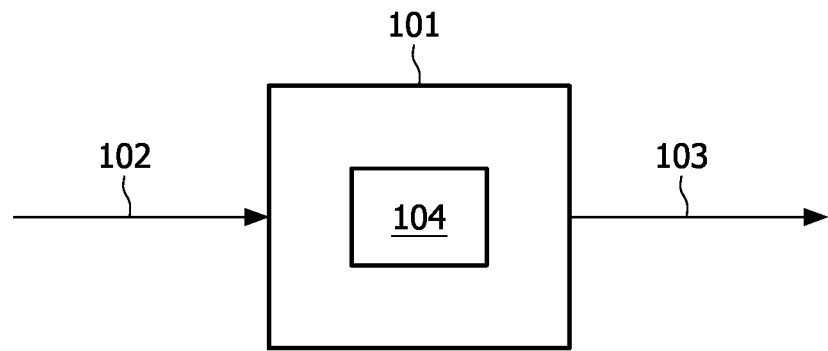
FIG. 1 shows a medical apparatus for determining estimated biological markers.

FIG. 1 shows a medical apparatus 101 for determining an estimated biological marker from a measured biological marker. The medical apparatus 101 comprises an input 102 for receiving input data representing at least the measured biological marker and an output 103 for providing the estimated marker. The medical apparatus 101 comprises a processing unit 104 which is able to process the input data using a biological model for determining the estimated biological marker. The processing unit 104 may be a computer, an electronic circuit board or other electronic device capable of processing the biological model which may be in the form of a computer program or an algorithm. The received input data may provided directly to the processing unit 104. Alternatively, the input data may be conditioned and/or converted, for example by an analogue-to-digital converter, before being provided to the processing unit 104. The processing unit 104 uses the input data in connection with the biological model for determining or deriving estimated biological markers.

The biological marker, or biomarker, is a biological substance which is can be used in the process of making a diagnosis of a patient or for estimating a patient condition. For example, the detection of an increased level of a protein in blood may be used as an indication of an infection. Accordingly, a measurement resulting in a determination of a presence, non-presence, concentration, change of concentration of a biological marker can be used as an intermediate result for use in making a diagnosis or for estimating a patient condition.

Various biological markers are known to be useful for helping in making a diagnosis. Biological markers should not only be understood at biological entities such as proteins. That is, biological markers may also comprise data obtained from analysis of biological material, for example gene copy numbers obtained from analysis of genetic material. Thus, biological markers comprise proteins, metabolites, genetic polymorphisms, gene copy number variations, or any other molecular entity that can be correlated with the protein state, its isoforms or the protein complex. A Biological marker is also known as any molecular substance that is an indicator of a biological state.

The measured biological marker may be obtained from analyzing a biological sample obtained and removed from the patient. Accordingly, the analysis of the biological sample neither requires interaction with a patient's body nor involvement of a medical practitioner. However, this does not exclude the possibility that the measured input data may have been obtained by analyzing biological substances on the patient, for example by the use of a micro bio-assay implemented on or in the body. Accordingly, the measured biological marker may represent a presence, a non-presence, a concentration or a change of concentration of a biological marker.

Similarly, the estimated biological marker may be in the form of a presence, a non-presence, a concentration or a change of concentration of a biological marker.

It is understood that one or more measured biological markers may be used for determining one or more estimated biological markers. For example, the measurement of protein A and/or B can be used for determining an estimated protein C and/or D. For example, the following three biological markers may be measured relatively easy in a clinical environment (in vitro): the prothrombin activation product (F1+2), the coagulation factor V in blood and antithrombin III (inhibitor of the thrombin). However, in order to provide enough clinical information for assisting the clinician in deciding on a patient diagnosis or patient condition, it would be beneficial to have information about what the most probable final concentration of the marker, thrombin, would be under such conditions. Here "final" refers to the concentration of the thrombin that is generated under steady-state conditions. However, since thrombin is cannot be easily measured due to the difficulties in detection, it would be of great advantage if the thrombin could be estimated on basis of the three measured biological markers. For example, the measured biological markers and the estimated thrombin may be used as intermediate results, possibly in combination with other patient data, for assisting in evaluating the risk of bleeding or Deep Venous Thrombosis.

A patient should be understood broadly as any human or animal that may suffer from a disease or may be healthy.

In this description estimating a patient condition must be understood broadly. Thus, a patient condition may be a diagnosis of a particular disease (e.g. early diagnosis of bleeding), an estimated likelihood of survival, an estimated time before death, a suggestion for a particular treatment, likelihood for a positive outcome of a particular treatment, stage of a disease. Also a patient condition may be the effect on particular biological markers or other biological substances caused by a treatment, for example drugs given to the patient.

Within the context of this description the a clinician is to be understood broadly as equivalently referring to a care giver, a healthcare person, a physician, a nurse, a technician, or a hospital administrator.

Furthermore, a patient condition may be accompanied with a percentage indicating an estimated certainty of the one or more estimated patient conditions.

Figure 2:
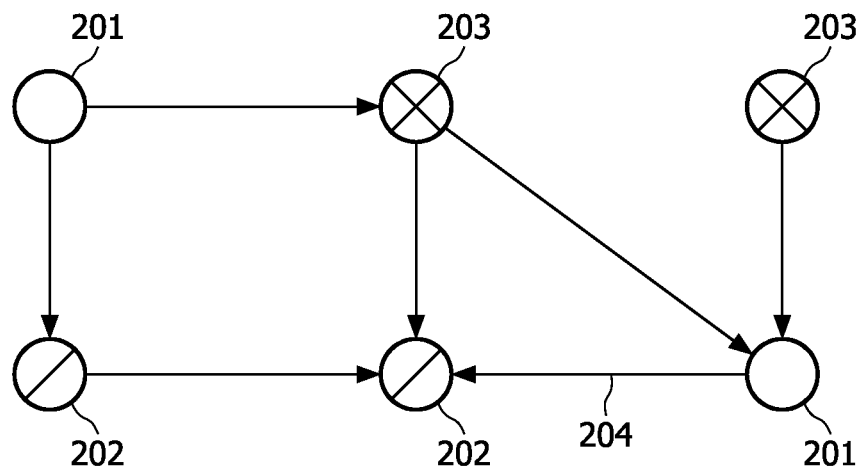
FIG. 2 illustrates the method of determining estimated biological markers.

FIG. 2 illustrates the method of determining estimated biological markers 202 by using measured biological markers 201. In this example, the measurement of the two markers 201 enables estimation of other two markers 202. The other two markers 203 are either not possible to estimate since insufficient measured data are available for making a sufficient accurate estimation, or the other two markers 203 are not interesting to estimate since the markers 203 are not useful for estimating a patient condition. FIG. 2 illustrates the principle behind a biological model used for estimating biological markers. That is, the biological model may be a physical model which models the relations and interactions between various biological markers; for example a concentration or presence of one biological marker 201 may imply a concentration or presence of another biological marker 202. Such relations, which are illustrated by connections 204 in FIG. 2, may be known from experimental or theoretical studies of biological markers.

The biological model of the interactions between biological markers may be obtained from existing knowledge. However, the model may also be adapted to include recent measurements of biological markers and other clinical trial data, for example comprising age, sex, current or previous diseases, current or previous therapies, dosages of therapeutic drugs and measured clinical data (e.g. genetic measurements). Accordingly, in an embodiment the biological model is an adaptive model which can be optimized for a particular patient by adapting the model with recent biological measurements and clinical data.

More specifically, the model may be designed so as to describe interactions between proteins, their isoforms and complexes. The model may additionally describe the kinetic properties and normal concentrations of proteins, their iso forms and complexes. The model may additionally describe small molecules, known as cofactors. As mentioned previously, the model may additionally describe the relations between clinical data and physiological concentrations (e.g. concentrations of markers), kinetic parameters, protein activities, complex stability and others.

The physical biological model may use sets of differential equations for describing the dynamics of for example biological markers.

Instead of using a model based on differential equations, the biological model may be established using a linear discriminant, a neural network, a Bayesian network or other deterministic or stochastic models. Clearly, the biological model may be obtained by combining physical, other deterministic models and stochastic models.

The use of clinical data, for example the age of a patient, makes it possible to estimate biological parameters with higher accuracy. For example, a biological model which does not include clinical data may generate several estimates of biological markers; for example different estimated concentrations of markers or different estimated types of biological markers. This may be caused by an underdetermined model. In an embodiment, in order to preclude some of the several results, application of clinical data in the model may be used. For example, by applying the knowledge of a therapy in the model, some of the several estimated results may be precluded—so that only the correct estimations are left back. Alternatively, the application of additional clinical data may not be used in the biological model, but may be applied subsequent to estimating biological markers for precluding some of the estimated markers.

In an embodiment, several biological models are used, where each biological model serves to model particular clinical data. For example, one biological model may model the marker's interactions of a patient suffering from a particular disease, and a second biological model may model the marker's interactions of a patient suffering from another particular disease. Thus, with the knowledge of the patient's disease, the most suitable biological model can be selected.

In order to increase the accuracy of estimated or predicted biological markers, the medical apparatus may be successively provided with input data in order to provide the biological model with a history of input data. When the biological model is provided with a sequence of input data, where the most recent input data is separated in time from the previous input data, the biological model can estimate or predict biological markers with higher accuracy since the model is, so to say, tuned into the specific patient. That is, since patients are different but the same general biological model may for used for such different patients the model is gradually adapted to a specific patient when more and more input data are provided.

It is understood that the method of repeated updating the biological model with new input data may comprise updating the model with both measured biological markers, clinical data and measured clinical data.

The biological model comprises parameters, for example parameters relating to the kinetics of biological markers or the relations 204 between different markers. In an embodiment, those parameters are initially set to values that match an average patient. In order to adapt the biological model to a specific patient, those parameters may be adapted to the specific patient by using a least a fraction of the history of input data and clinical data—for example the ten most recent input data and clinical data may be used. It is known to use minimization methods (e.g. root-mean-square) in order minimize the error between model predictions and actual measured values. For example, the biological model can be used to also predict biological markers 201 (which are also measured) so that the error between predicted markers 201 and the same measured markers 201 can be minimized so as to adapt the parameters of the model to the patient.

For example, the amount of thrombin that is generated in blood can be estimated using several measurements of prothrombin activation peptide (F1+2), Factor V concentration and amount of anthithrombin III. Such estimation, based on only one measurement might not be sufficient and, therefore, another measurement of the same parameters might be performed after a certain time interval (taking into account the medications that have been admitted). The improved estimation of thrombin markers obtained using both the first and the second, and possible more, measured markers can be used in combination with other patient data for assisting in evaluating the risk of bleeding or Deep Venous Thrombosis using a patient condition model (described below). Such measurements can also be performed specifically after infusion (admission) of different doses of medication (drug) and the results can be monitored in time, thereby utilizing the knowledge of what the effect of such medication on the proteins is—that is, the effect of the drug on the medical model is known and, thereby, gives extra information on what particular specificities exists for a biological sample.

Figure 3:
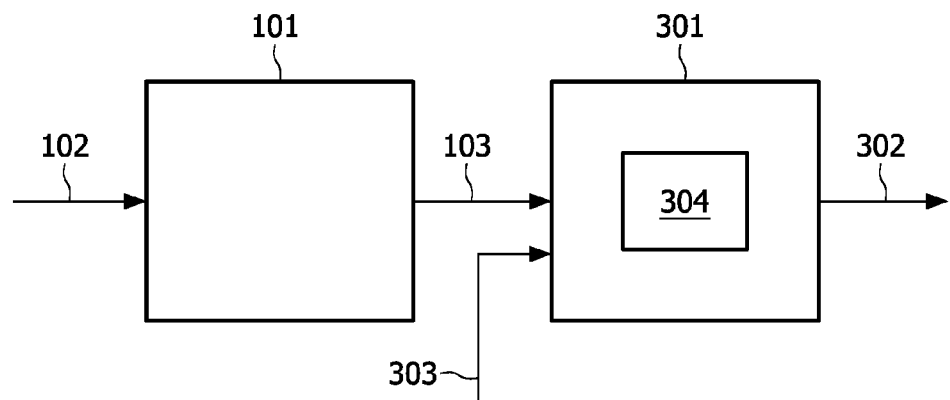
FIG. 3 shows an embodiment of the invention where the medical apparatus provides estimated biological markers to a patient condition apparatus 301.

FIG. 3 shows an embodiment of the invention where the estimated biological marker determined by the medical apparatus 101 is provided to a patient condition apparatus 301, for example via output 103. Other data comprising clinical data and measured biological markers may also be provided via output 103 or some other input 303. The a patient condition apparatus 301 comprises processing means 304—for example a computer, a processor or a electronic circuit board—for estimating a patient condition using patient data. Patient condition was defined previously. Patient data is defined as comprising one or more of the measured biological marker, the estimated biological marker and clinical data, where clinical data comprises non-measurable values (e.g. age, sex, therapies, etc.) and measurable values (e.g. blood pressure). The estimation of the patient conditions comprises processing the patient data using a patient condition model which relates the patient data to patient conditions. The determined patient condition may be provided via output means 302.

It is known to use patient condition models for extraction information from patient data which may be used for predicting various patient conditions. Such models may be based on deterministic models, for example physical models based on ordinary differential equations, or such models may be based on stochastic models, or combinations thereof.

Figure 4:
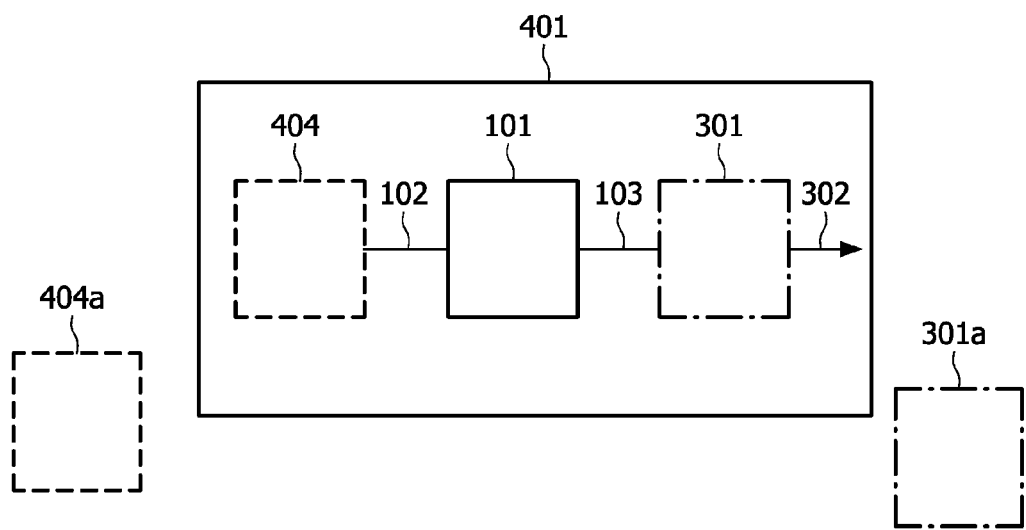
FIG. 4 shows a clinical system comprising the medical apparatus and the patient condition apparatus.

FIG. 4 shows a clinical system 401 according to an embodiment of the invention. The clinical system comprises the medical apparatus 101 according to FIG. 1 and patient condition apparatus 301. It is understood that the patient condition apparatus 301 and medical apparatus 101 may be integrated into a single unit 401. The patient condition apparatus 103 may also be integrated into the medical apparatus 101, for example so that the patient condition apparatus 301 and medical apparatus 101 shares the same processing unit 104. Alternatively, the clinical system 401 may comprise the medical apparatus 101 and the stand-alone patient condition apparatus 301a which is placed externally to the medical apparatus 101, but connectable with the medical apparatus 101.

Any of the output 103 for providing the estimated marker and the output 302 for providing the patient condition may be an electric output terminal or internet connection capable of providing a digital or analogue signal representing the estimated markers and patient conditions. Alternatively, or additionally, any of the outputs 103,302 may be an output device for visualizing estimated markers or patient conditions, for example a monitor, a computer or a printer.

The input 102 for receiving input data representing the measured biological marker may be an electric input terminal, a network connection or an internet connection. It is understood that the patient condition apparatus 301 may comprise an input terminal similar to the input 102 for receiving estimated biological markers and/or other patient data.

The clinical system 401 may further comprise an analyzing unit 404 for analyzing biological samples of a patient for generating measured data of biological markers. The analyzing unit 404 may for example be a bio-assay. The analyzing unit 404 may be integrated into the clinical system 401. Alternatively, the clinical system 401 may comprise the medical apparatus 101 and a stand-alone analyzing unit 404a which is placed externally to the medical apparatus 101, but connectable with the medical apparatus 101. The analyzing unit 404 may for example be adapted for receiving samples of blood which can be analyzed for providing measured biological markers to the medical apparatus 101. The analyzing of for example blood samples for measurements of concentrations of biological markers may be performed by the use of a chemical initiator, which is known in the art.

The clinical system 401 may further comprise a graphical user interface (not shown) that enables a clinician to provide information to the clinical system. The user interface may comprise a keyboard, pointing devices and a monitor. The user interface enables the clinician to enter information relating to patient data comprising age, sex, therapies, etc.

The analyzing unit 404, 404a may generate analysis results that are interpreted by the clinician by visual inspection of the analyzing unit 404. For example, the analysis result may be visually provided as a color change, or other visual change. Such visual analysis results may be entered into the clinical system 401 of FIG. 4 by use of the graphical user interface. Such analysis results and other patient data may also be entered into the medical apparatus 101 when the medical apparatus 101 is provided with a graphical user interface.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A method for determining an estimated first biological marker of a subject from a measured second biological marker and clinical data of the subject, the method comprising the acts of:
   determining an error between a selected measured marker of the subject and a predicted value of the selected measured marker predicted by a biological model;
   adapting the parameters of the biological model to the subject by minimizing the error;
   receiving input data representing the measured second biological marker;
   processing the input data using the biological model having the adapted parameters for determining a plurality of estimations including the estimated first biological marker from the measured second biological marker, wherein the estimated first biological marker is different from the measured second biological marker, and wherein the biological model models relations between biological markers including the first and second biological markers;
   determining incorrect estimations included in the plurality of estimations based on the clinical data of the subject;
   precluding the incorrect estimations from the plurality of estimations to result in corrected estimations;
   determining the estimated first marker from the corrected estimations; and
   providing the estimated first marker via an output device for rendering the estimated first marker on the output device.

2. The method according to claim 1, wherein the biological marker is selected from the list comprising: proteins, metabolites, genetic polymorphisms, gene copy number variations, or any other molecular entity that can be correlated with the end protein state, its isoforms or the protein complex.

3. The method according to claim 1, wherein the biological model is configured to model kinetic interactions between biological markers.

4. The method according to claim 1, wherein the clinical data is selected from a group consisting of: age, sex, current or previous diseases, current or previous therapies, dosages of therapeutic drugs, and measured biological factors of the subject.

5. The method according to claim 1, wherein the receiving act comprises receiving first input data and receiving second input data, wherein the first and second input data are received at different points in time.

6. The method according to claim 1, wherein the measured biological marker is a concentration of a biological marker, alternatively a change in the concentration of the biological marker.

7. The method according to claim 1, wherein the estimated biological marker is a concentration of the biological marker, alternatively a change in the concentration of the biological marker.

8. The method according to claim 1, further comprising the act of:
   estimating a patient condition of the subject using patient data comprising one or more of the measured biological marker, the estimated biological marker and the clinical data, wherein the estimation of the patient condition comprises processing said patient data using a patient condition model relating said patient data to patient conditions.

9. A non-transitory computer readable medium embodying computer instructions which, when executed by a processor, configure the processor to perform the method of claim 1.

10. The method of claim 1, wherein the output device is one of a display device and a printer.

11. The method of claim 1, wherein the receiving act further comprises receiving a plurality of input data at different points in time to form a history of input data, and wherein the processing act processes the history along with new input data when the new input data is received.

12. The method of claim 11, prior to the act of determining an error, further comprising the acts of:
   setting the parameters to match an average patient; and
   adapting the parameters of the biological model to the subject using the clinical data of the subject and the history of input data.

13. The method of claim 1, wherein the measured biological marker of the subject includes at least one of prothrombin activation product, coagulation factor V, and antithrombin, and the estimated biological marker comprises thrombin.

14. The method of claim 1, prior to the act of determining an error, further comprising the acts of:
   setting the parameters to match an average patient; and
   adapting the parameters of the biological model to the subject using the clinical data of the subject, clinical data including at least one of age, sex, current or previous diseases, current or previous therapies, dosages of therapeutic drugs, and measured biological factors of the subject.

15. A medical apparatus for determining an estimated first biological marker from a measured second biological marker, the apparatus comprising:
   an input for receiving input data representing the measured second biological marker;
   a processing unit configured to:
      determining an error between a selected measured marker of a subject and a predicted value of the selected measured marker predicted by a biological model;
      adapting the parameters of the biological model to the subject by minimizing the error;
      process the input data using the biological model having the adapted parameters for determining a plurality of estimations including the estimated first biological marker from the measured second biological marker, wherein the estimated first biological marker is different from the measured second biological marker, and wherein the biological model models relations between biological markers including the first and second biological markers;
      determine incorrect estimations included in the plurality of estimations based on the clinical data of the subject;
      preclude the incorrect estimations from the plurality of estimations to result in corrected estimations; and
      determine the estimated marker from the corrected estimations; and
   an output for providing the estimated first biological marker.

16. The medical apparatus of claim 15, further comprising at least one of a display device and a printer connected to the output for rendering the estimated biological marker.

17. The medical apparatus of claim 15, wherein the measured biological marker of the subject includes at least one of prothrombin activation product, coagulation factor V, and antithrombin, and the estimated biological marker comprises thrombin.

18. A clinical system for estimating a patient condition, the clinical system comprising:

a medical apparatus for determining an estimated first biological marker from a measured second biological marker, the medical apparatus comprising:
  an input for receiving input data representing the measured second biological marker;
  a processing unit configured to:
  determine an error between a selected measured marker of a subject and a predicted value of the selected measured marker predicted by a biological model;
  adapt the parameters of the biological model to the subject by minimizing the error;
  process the input data using the biological model having the adapted parameters for determining a plurality of estimations including the estimated first biological marker from the measured second biological marker, wherein the estimated first biological marker is different from the measured second biological marker, and wherein the biological model models relations between biological markers including the first and second biological markers;
  determine incorrect estimations included in the plurality of estimations based on the clinical data of the subject;
  preclude the incorrect estimations from the plurality of estimations to result in corrected estimations; and
  determine the estimated marker from the corrected estimations; and
  an output for providing the estimated first biological marker;
a patient condition apparatus comprising a further processor configured to perform an estimation a patient condition of the subject using patient data comprising one or more of the measured biological marker, the estimated biological marker and the clinical data, wherein the estimation of the patient condition comprises processing said patient data using a patient condition model relating said patient data to patient conditions; and
an output for providing the patient condition.

19. The clinical system of claim 18, further comprising at least one of a display device and a printer connected to the output for rendering the estimated biological marker.

20. The clinical system of claim 18, wherein the measured biological marker of the subject includes at least one of prothrombin activation product, coagulation factor V, and antithrombin, and the estimated biological marker comprises thrombin.

* * * * *